United States Patent
Simpson

(10) Patent No.: US 8,900,836 B2
(45) Date of Patent: Dec. 2, 2014

(54) ACID PRODUCTION BY FERMENTATION

(71) Applicant: LanzaTech New Zealand Limited, Roselle, IL (US)

(72) Inventor: Sean Dennis Simpson, Auckland (NZ)

(73) Assignee: Lanzatech New Zealand Limited, Auckland (NZ)

( * ) Notice: Subject to any disclaimer, the term of this patent is extended or adjusted under 35 U.S.C. 154(b) by 0 days.

(21) Appl. No.: 13/720,281

(22) Filed: Dec. 19, 2012

(65) Prior Publication Data

US 2013/0109066 A1 May 2, 2013

Related U.S. Application Data

(63) Continuation of application No. 13/121,426, filed as application No. PCT/NZ2011/000033 on Mar. 10, 2011, now abandoned.

(60) Provisional application No. 61/312,596, filed on Mar. 10, 2010.

(51) Int. Cl.
| | |
|---|---|
| C12P 7/56 | (2006.01) |
| C12N 9/00 | (2006.01) |
| C12N 1/20 | (2006.01) |
| C12N 15/00 | (2006.01) |
| C07H 21/04 | (2006.01) |

(52) U.S. Cl.
CPC ........................... C12P 7/56 (2013.01)
USPC ..... 435/139; 435/183; 435/252.3; 435/320.1; 536/23.2

(58) Field of Classification Search
None
See application file for complete search history.

(56) References Cited

U.S. PATENT DOCUMENTS

| | | |
|---|---|---|
| 5,173,429 A | 12/1992 | Gaddy et al. |
| 5,593,886 A | 1/1997 | Gaddy |
| 5,753,474 A | 5/1998 | Ramey |
| 5,807,722 A | 9/1998 | Gaddy |
| 5,821,111 A | 10/1998 | Grady et al. |
| 6,136,577 A | 10/2000 | Gaddy |
| 6,340,581 B1 | 1/2002 | Gaddy |
| 6,368,819 B1 | 4/2002 | Gaddy et al. |
| 6,753,170 B2 | 6/2004 | Gaddy et al. |
| RE39,175 E | 7/2006 | Gaddy et al. |
| 7,196,218 B2 | 3/2007 | Gaddy et al. |
| 7,285,402 B2 | 10/2007 | Gaddy et al. |
| 2007/0178569 A1 | 8/2007 | Leschine et al. |
| 2007/0275447 A1 | 11/2007 | Lewis et al. |
| 2010/0323417 A1 | 12/2010 | Simpson et al. |

FOREIGN PATENT DOCUMENTS

| | | |
|---|---|---|
| EP | 1281766 | 6/2008 |
| WO | 2008028055 | 3/2008 |
| WO | 2008154301 | 12/2008 |
| WO | 2009020747 | 2/2009 |
| WO | 2009058028 | 5/2009 |
| WO | 2010093262 | 8/2010 |
| WO | 2011002318 | 1/2011 |

OTHER PUBLICATIONS

Ezeji et al. Curr Opin Biotechnol. Jun. 2007;18(3):220-7. Epub Apr. 25, 2007.*
Germain et al. Applied Microbiology and Biotechnology (1986), 24(4), 300-5.*
Phillips et al. "Synthesis Gas as Substrate for the Biological Production of Fuels and Chemicals" Applied Biochemistry and Biotechnology, 45(1), 145-157.
Abrini et al. "*Clostridium autoethanogenum*, sp. Nov., an anaerobic bacterium that produces ethanol from carbon monoxide" Archives of Microbiology, 161(4), 345-351(1994).
Ragsdale, Stephen W "Life with Carbon Monoxide" Critical Reviews in Biochemistry and Molecular Biology, 39: 165-195, 2004.
Henstra et al."Microbiology of synthesis gas fermentation for biofuel production" Current Opinion in Biotechnology, 18(3), 200-206 (2007).
Heiskanen, H et al; "The effects of syngas composition on the growth and product formation of *Butyribacterium methylotrophicum*"; Enzyme and Microbial Technology (2007) vol. 41, pp. 362-367.
Dabrock, B et al. "Parameters Affecting Solvent Production by *Clostridium pasteurianum*"; Applied and Environmental Microbiology (1992) vol. 58(4), pp. 1233-1239.
Meyer, C.L et al; "Carbon monoxide gasing leads to alcohol production and butyrate uptake without acetone formation in continuous cultures of *Clostridium acetobutylicum*"; Appl Microbiology Biotechnology (1986) vol. 24, pp. 159-167.
Villano et al., Bioelectrochemcial reduction of CO2 to CH4 via direct and indirect extracellular electron transfer by a hydrogenophilic methanogenic culture, Bioresource Technology, vol. 101, Jan. 13, 2010, pp. 3085-3090.
Cheng et al., Direct biological conversion of electrical current into methane by electromethanogenesis, Environmental Science and Technology, vol. 43, (2009), pp. 3953-3958.
Jeon et al., Production of ethanol directly from potato starch b mixed culture of *Saccharomyces cerevisiae* and *Aspergillus niger* using electrochemical bioreactor, Journal of Microbiology and Biotechnology, vol. 18, (2008), p. 545-551.
European Search Report (EP11733140) dated Sep. 12, 2013.

* cited by examiner

*Primary Examiner* — Christian Fronda
(74) *Attorney, Agent, or Firm* — Frank S Molinaro

(57) ABSTRACT

The invention provides methods for producing Lactate by anaerobic Fermentation. According to particular methods of the invention, Lactate is produced by anaerobic fermentation of a substrate comprising hydrogen and carbon monoxide.

8 Claims, 4 Drawing Sheets

ACID PRODUCTION BY FERMENTATION

CROSS REFERENCE TO RELATED APPLICATIONS

This application is a continuation of pending U.S. application Ser. No. 13/121,426 filed on 8 Sep. 2011 which in turn is a National Stage of International Application No. PCT/NZ2011/000033, filed on Mar. 10, 2011, which claims the benefit of the priority date of U.S. Provisional Application No. 61/312,596 filed Mar. 10, 2010. The content of all of which applications mentioned above are incorporated herein by reference in their entirety.

FIELD OF THE INVENTION

This invention relates to the production of lactate by microbial fermentation of substrates comprising CO.

BACKGROUND OF THE INVENTION

Lactic acid is an important platform chemical with many applications. Over the last decade, lactic acid has gained importance in the detergence industry. Lactic acid has descaling as well as anti-bacterial properties, so has been used as an environmentally beneficial cleaning product. Furthermore, lactic acid is a precursor for several biodegradable polymers such as polylactic acid. These types of plastics provide a good option for substituting conventional plastics produced from petroleum oil because of low CO2 emissions. Other applications include precursors for lactate esters, which can replace petrochemical derived solvents.

Lactic acid is typically produced by fermentation of carbohydrates such as glucose, fructose and sucrose. The most commercially important genus of lactic acid fermenting bacteria is *Lactobacillus*, though other bacteria and even yeast are also used. In such fermentations, lactic acid is formed through the reduction of pyruvate, which is in turn produced by glycolysis. The cost of these carbohydrate feed stocks is influenced by their value as human food or animal feed. For example, cultivation of starch or sucrose-producing crops for lactic acid production is not economically sustainable in all geographies. Therefore, it is of interest to develop technologies to convert lower cost and/or more abundant carbon resources into lactic acid.

Carbon Monoxide (CO) is a major by-product of the incomplete combustion of organic materials such as coal or oil and oil derived products. Although the complete combustion of carbon containing precursors yields CO2 and water as the only end products, some industrial processes need elevated temperatures favouring the build up of carbon monoxide over CO2. One example is the steel industry, where high temperatures are needed to generate desired steel qualities. For example, the steel industry in Australia is reported to produce and release into the atmosphere over 500,000 tonnes of CO annually.

Furthermore, CO is also a major component of syngas, where varying amounts of CO and H2 are generated by gasification of a carbon-containing fuel. For example, syngas may be produced by cracking the organic biomass of waste woods and timber to generate precursors for the production of fuels and more complex chemicals.

The release of CO into the atmosphere may have significant environmental impact. In addition, emissions taxes may be required to be paid, increasing costs to industrial plants. Since CO is a reactive energy rich molecule, it can be used as a precursor compound for the production of a variety of chemicals. However, this valuable feedstock has not been utilised to produce lactic acid.

It is an object of the present invention to provide a process that goes at least some way towards overcoming the above disadvantages or at least to provide the public with a useful choice.

STATEMENT OF INVENTION

In one aspect, the invention provides a method of producing lactic acid by microbial fermentation of a substrate comprising carbon monoxide. In particular embodiments, the invention provides a method of producing lactic acid by microbial fermentation, the method including:
 a. providing a substrate comprising CO;
 b. in a bioreactor containing a culture of one or more micro-organisms, anaerobically fermenting the substrate to produce lactic acid.

In particular embodiments, at least 0.05 g/day lactic acid per Liter of fermentation broth is produced. In particular embodiments, at least 0.1 g/L/day; or at least 0.2 g/L/day; or at least 0.3 g/L/day; or at least 0.5 g/L/day; or at least 1.0 g/L/day lactic is produced.

In another aspect, the invention provides a method of increasing efficiency lactic acid production by fermentation, the method including:
 a. providing a substrate comprising CO;
 b. in a bioreactor containing a culture of one or more micro-organisms, anaerobically fermenting the substrate to produce lactic acid.

In another aspect of the invention, there is provided a method of producing lactic acid by microbial fermentation, the method including:
 a. providing a substrate
 b. in a bioreactor containing a culture of one or more micro-organisms, anaerobically fermenting the substrate, wherein one or more micro-organisms includes one or more lactate dehydrogenase genes;
 c. up-regulating the lactate dehydrogenase gene(s), such that lactic acid is produced by the micro-organism(s).

In particular embodiments, the substrate comprises CO.

In particular embodiments of the various aspects, the substrate comprising carbon monoxide is a gaseous substrate comprising carbon monoxide. The gaseous substrate comprising carbon monoxide can be obtained as a by-product of an industrial process. In certain embodiments, the industrial process is selected from the group consisting of ferrous metal products manufacturing, non-ferrous products manufacturing, petroleum refining processes, gasification of biomass, gasification of coal, electric power production, carbon black production, ammonia production, methanol production and coke manufacturing. In one embodiment the gaseous substrate comprises a gas obtained from a steel mill. In another embodiment the gaseous substrate comprises automobile exhaust fumes.

In particular embodiments, the CO-containing substrate typically contains a major proportion of CO, such as at least about 20% to about 100% CO by volume, from 40% to 95% CO by volume, from 40% to 60% CO by volume, and from 45% to 55% CO by volume. In particular embodiments, the substrate comprises about 25%, or about 30%, or about 35%, or about 40%, or about 45%, or about 50% CO, or about 55% CO, or about 60% CO by volume. Substrates having lower concentrations of CO, such as 6%, may also be appropriate, particularly when $H_2$ and $CO_2$ are also present.

In particular embodiments of the various aspects, the substrate comprising CO is provided at a sufficient level, such that lactic acid is produced. In particular embodiments, CO is provided such that a specific uptake rate of at least 0.4 mmol/g/min; or at least 0.5 mmol/g/min; or at least 0.6 mmol/g/min; or at least 0.7 mmol/g/min; or at least 0.8 mmol/g/min; or at least 0.9 mmol/g/min; or at least 1.0 mmol/g/min; or at least 1.2 mmol/g/min; or at least 1.5 mmol/g/min is maintained.

In certain embodiments of the various aspects, the method comprises microbial fermentation using one or more carboxydotrophic microorganisms via the Wood-Ljungdahl pathway. In particular embodiments, the microorganism is a clostridia, such as *Clostridium autoethanogenum*.

In another aspect, the invention provides a method of producing lactic acid by microbial fermentation, the method including:
  a. providing a substrate
  b. in a bioreactor including a culture of *Clostridium autoethanogenum*, anaerobically fermenting the substrate to produce lactic acid.

In particular embodiments, the substrate is one or more carbohydrates such as fructose. Alternatively the substrate is a substrate comprising carbon monoxide, more preferably a gaseous substrate comprising carbon monoxide, as herein before described In a further aspect of the invention, there is provided a method according to any of the previous aspects, wherein the method further includes the step of capturing or recovering the lactic acid.

In a further aspect, there is provided lactic acid produced by the methods of any of the previous aspects.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

FIGURES

Figure 5A:
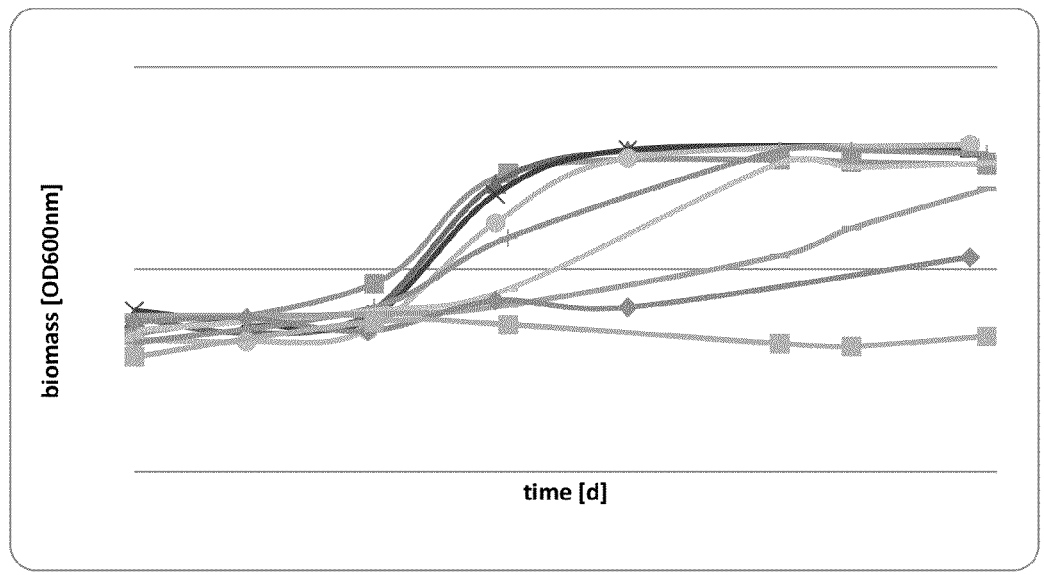
Figure 5B:
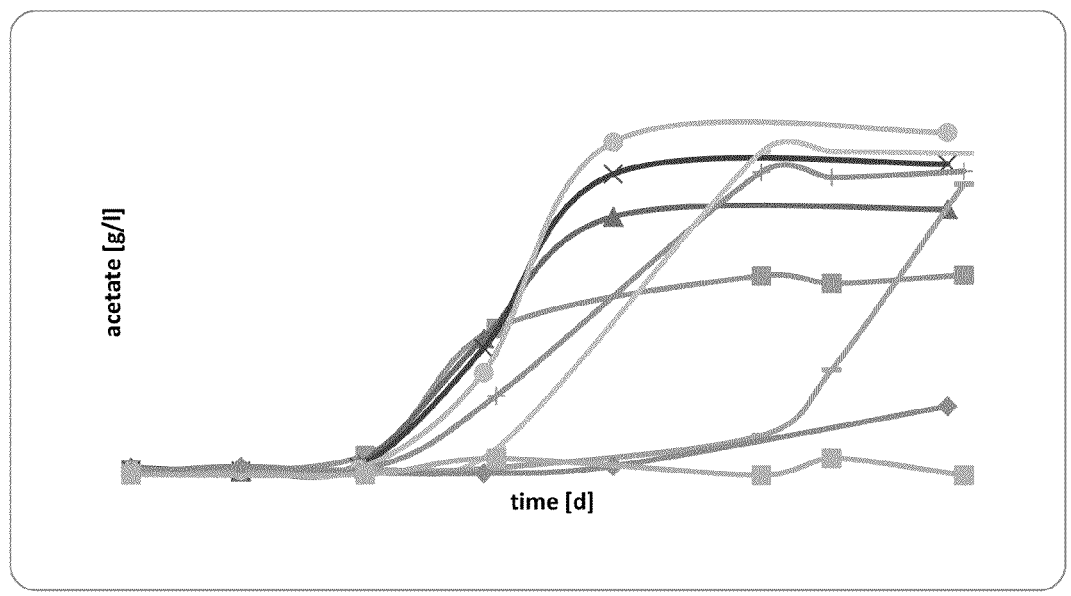
Figure 5C:
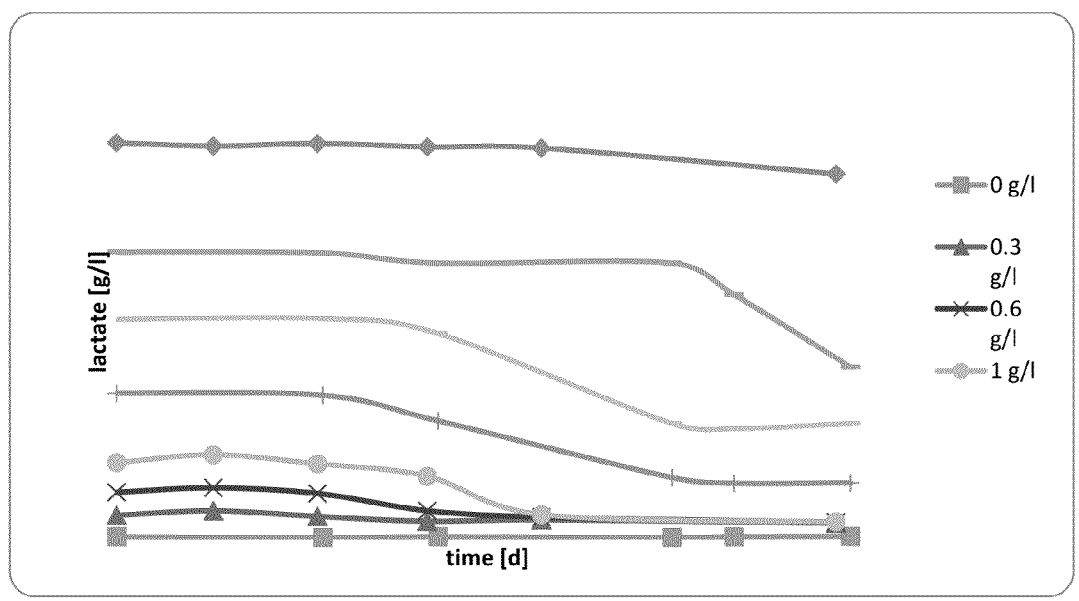

FIG. 5a, FIG. 5b, and FIG. 5c are graphs showing the effects of differing lactate concentrations on cell growth and metabolite production as described in example 5. The figure legend on FIG. 5c also relates to FIGS. 5a and 5b.

DETAILED DESCRIPTION OF THE INVENTION

The following is a description of the present invention, including preferred embodiments thereof, given in general terms. The invention is further exemplified in the disclosure given under the heading "Examples" herein below, which provides experimental data supporting the invention, specific examples of aspects of the invention, and means of performing the invention.

The terms 'lactic acid' and 'lactate' have been used herein interchangeably and include all steroisomers of 2-hydroxy propionic acid including (R), (S) and racemic forms.

The term "bioreactor" includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas Lift Fermenter, Static Mixer, or other vessel or other device suitable for gas-liquid contact. As is described herein after, in some embodiments the bioreactor may comprise a first growth reactor and a second fermentation reactor. As such, when referring to the addition of a substrate, for example a substrate comprising carbon monoxide, to the bioreactor or fermentation reaction it should be understood to include addition to either or both of these reactors where appropriate.

The term "substrate comprising carbon monoxide" and like terms should be understood to include any substrate in which carbon monoxide is available to one or more strains of bacteria for growth and/or fermentation, for example.

"Gaseous substrates comprising carbon monoxide" include any gas which contains a level of carbon monoxide. The gaseous substrate will typically contain a major proportion of CO, preferably at least about 15% to about 95% CO by volume.

Unless the context requires otherwise, the phrases "fermenting", "fermentation process" or "fermentation reaction" and the like, as used herein, are intended to encompass both the growth phase and product biosynthesis phase of the process.

The inventors have surprisingly shown that lactic acid can be produced by microbial fermentation of a substrate comprising CO. It has been surprisingly shown that lactic acid can be produced by carboxydotrophic bacteria by fermentation of a substrate comprising CO. The inventors have found that fermentation produces several products whereby ethanol and lactic acid are significant substituents. Lactic acid has not been previously identified as a product of fermentation of a substrate comprising CO. In accordance with the methods of the invention, it has also been surprisingly demonstrated that lactic acid can be produced by *Clostridium autoethanogenum* from substrates comprising CO, particularly gaseous substrates comprising CO. The use of a gaseous carbon source, particularly a source including CO, in fermentation processes has not previously resulted in the production of lactic acid.

In particular embodiments of the invention, the efficiency of lactic acid production can be increased by providing the substrate at a sufficient level such that lactic acid is produced. It has been recognised that increasing the amount of substrate provided to a microbial culture, increases the amount of lactic acid produced by the culture.

In particular embodiments of the invention, the substrate comprising CO is provided at a sufficient level such that lactic acid is produced. It has been shown that a microbial culture comprising *C. autoethanogenum* can uptake CO at a rate up to approximately 1.0 to 2 mmol/gram dry weight microbial cells/minute (specific CO uptake). In particular embodiments of the invention, a substrate comprising CO is provided to the microbial culture comprising *C. autoethanogenum* such that a specific uptake is maintained substantially at or at least 0.4 mmol/g/min; or at least 0.5 mmol/g/min; or at least 0.6 mmol/g/min; or at least 0.7 mmol/g/min; or at least 0.8 mmol/g/min; or at least 0.9 mmol/g/min; or at least 1.0 mmol/g/min; or at least 1.2 mmol/g/min; or at least 1.5 mmol/g/min. In such embodiments, lactic acid is a significant fermentation product of at least 0.05 g/L; or at least 0.1 g/L; or at least 0.2 g/L; or at least 0.3 g/L; or at least 0.4 g/L; or at least 0.5 g/L. In particular embodiments, lactic acid is produced at a rate of at least 0.5 g/L/day; or at least 1 g/L/day.

In particular embodiments of the invention, apparatus used for conducting methods of the invention enable measurement and/or control of parameters such as CO supply, CO uptake, biomass level, pH, lactic acid production. For example, samples can be taken from a bioreactor to determine one or more of the above parameters and the bioreactor conditions optionally adjusted to improve lactic acid production. For example, in a bioreactor, wherein the microbial culture is producing no or insignificant amounts of lactic acid, the CO supply can be increased such that lactic acid is produced.

It is accepted that products such as acetate and ethanol are produced from CO via a combination of the acetyl-CoA cycle and the THF cycle via the Wood-Ljungdahl pathway as described in Phillips, J. R, et al, 1994, *Applied Biochemistry and Biotechnology*, 45/46: 145. However, in accordance with the methods of the invention, it has been surprisingly shown that lactic acid can be produced, particularly where CO is provided such that specific CO uptake rates of at least 0.4 mmol/g/min; or at least 0.5 mmol/g/min; or at least 0.6 mmol/g/min; or at least 0.7 mmol/g/min; or at least 0.8 mmol/g/min; or at least 0.9 mmol/g/min; or at least 1.0 mmol/g/min; or at least 1.2 mmol/g/min; or at least 1.5 mmol/g/min are maintained. Without wishing to be bound by theory, it is considered that by providing sufficient or elevated levels of CO, higher energy products, such as lactic acid can be produced during fermentation. It is considered precursors of products, such as lactic acid act as electron acceptors to relieve the microbial cell of excess reducing power, in the form of NAD (P)H, thus restoring a favourable NAD(P):NAD(P)H equilibrium. It is further considered that carbohydrates fermented by the culture can also be converted into lactic acid in a similar manner.

A putative NAD-dependent D-(−)-lactate dehydrogenase gene with a length of 981 bases could be identified in the genome sequence of *C. autoethanogenum* LZ1560 (strain deposited at DSMZ under the accession number 19630). The monocistronic gene shows high homology (74% identity (486/656), E-value 2e-55) to the partial D-(−)-lactate dehydrogenase gene IdhA of *Clostridium* sp. strains IBUN 13A (Accession Nr. GQ_180219.1) and IBUN 158B (Accession Nr. GQ_180219.1).

Nucleotide Sequence:

```
ATGAAAGTTTTGGCATATAGTCATAGACAAGATGAAACTGAATATTTCAAAAAATTCAG
TAAAAAATACGACGTGGAGGTTGTATTGTGTGATGATCCACCAACTATGGAAAATGCAG
ACTTGGCCAAGGGATTTGACTGCATCAGCATTATCACAACTAAAATTTCAGATAAATTA
GTAGAAAAATTTCATGAAATTGGAGTAAAATTTATATCTACAAGAACAATAGGATATGA
CCATATAGACATAAAAAAGGCAAAAGAGCTAGGTGTCCATATAGGCAATGTAAACTATT
CACCAAATAGTGTAGCCGATTATACAATTATGATGATTCTTATGGCTATAAGAAAAACG
AAAGCTATTATAGAACGAAGTAATGTACAGGATTATTCTTTAAAAGGTGTTCAAGGTAA
AGAGCTTCACAATTTAACTGTAGGTGTTATTGGTACAGGAAGAATTGGCCGTGCAGTTA
TAAGTCGCTTAAGTGGATTTGGCTGCAAAATATTAGCTTATGATTTATATGAGAATGAA
GAAATAAAGAAGTATGTTACATATGTTACACTAGAAGATCTCTTTAAAAACAGTGACAT
TATTACAATGCATGCACCTGCAACAGATGACAATTATCACATGATAAATAAGGATTCCA
TAGCACTTATGAAAGATGGTACATTTATTATCAATATAGCCCGAGGCTCACTTATCAAT
ACTGAAGATCTTATAGATGCCATTGAAAATAAAAAAATTGGTGGTGCAGCTATAGACGT
TATTGAAAATGAATTCGGACTTTGCTATAACGATTTAAAATGTGAGATACTAGATAAAA
GGGAAATGGCAATTTTAAAATCTTTTCCAAATGTAATTGTAACACCTCACACAGCTTTT
TATACAGATCAAGCTGTAAGTGATATGGTAGAACATTCTATTTTAAGTTGTGTTTTATT
CATGGAAGGCAAAGAAAATCCATGGCAAATTGAATAA
```

The gene encodes a protein of 321 amino acids, which has high homology to alpha keto acid dehydrogenases of other Clostridial species (see table 1), such as the lactate dehydrogenase of *C. acetobutylicum* which has exactly the same length. A COG (Clusters of Orthologous Groups of proteins) analysis assigns the protein to the functional group of 'lactate dehdrogenases and related dehydrogenases' (COG1052).

Protein Sequence:

```
MKVLAYSHRQDETEYFKKFSKKYDVEVVLCDDPPTMENADLAKGFDCISIITTKISDKL
VEKFHEIGVKFISTRTIGYDHIDIKKAKELGVHIGNVNYSPNSVADYTIMMILMAIRKT
KAIIERSNVQDYSLKGVQGKELHNLTVGVIGTGRIGRAVISRLSGFGCKILAYDLYENE
EIKKYVTYVTLEDLFKNSDIITMHAPATDDNYHMINKDSIALMKDGTFIINIARGSLIN
TEDLIDAIENKKIGGAAIDVIENEFGLCYNDLKCEILDKREMAIL KSFPNVIVTPHTA
FYTDQAVSDMVEHSILSCVLFMEGKENPWQIE*
```

Further evidence comes from a domain search carried out against PROSITE (Hulo N, et al, (2008) 'The 20 years of PROSITE' *Nucleic Acids Res* 36: D245-249) and Pfam (Finn et al (2010) 'The Pfam protein families database' *Nucleic Acids Res* 38: D211-222) databases. The PROSITE search yielded two strong hits for a 'D-isomer specific 2-hydroxy-acid dehydrogenases NAD-binding signature' (PS00065 and PS00671), while a 'D-isomer specific 2-hydroxyacid dehydrogenase, catalytic domain' and a 'D-isomer specific 2-hydroxyacid dehydrogenase, NAD binding domain' could be identified from the Pfam search with a high E-value of 8.1e-72 and 2.1e-30, respectively.

The protein is proposed to catalyze the reaction pyruvate+NADH to D-(−)-lactate+NAD$^+$ according to other NAD dependent D-(−)-lactate dehydrogenases (EC 1.1.1.28).

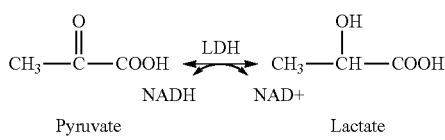

TABLE 1

Best protein BLAST (Altschul et al., (1990) 'Basic local alignment search tool' *J Mol Biol* 215: 403-410) hits for lactate dehydrogenase of *Clostridium autoethanogenum* LZ1560

| Description | Accession Nr. | Identity | E-value |
| --- | --- | --- | --- |
| D-isomer specific 2-hydroxyacid dehydrogenase, NAD-binding [*Clostridium beijerinckii* NCIMB 8052] | YP_001308638.1 | 73% (241/326) | 1e−143 |
| alpha-keto acid dehydrogenase [*Clostridium kluyveri* DSM 555] | YP_001395598.1 | 71% (233/325) | 1e−141 |
| lactate dehydrogenase [*Clostridium acetobutylicum* ATCC 824] | NP_348170.1 | 69% (226/325) | 1e−137 |
| D-specific alpha-keto acid dehydrogenase [*Clostridium butyricum* 5521] | ZP_02948009.1 | 67% (220/325) | 1e−130 |

It is considered lactate dehydrogenase can be upregulated in accordance with the methods of the invention. For example, where CO is supplied at sufficient levels, lactate dehydrogenase is upregulated. In particular, where CO is supplied such that the specific CO uptake by the microbial culture is at least 0.4 mmol/g/min; or at least 0.5 mmol/g/min; or at least 0.6 mmol/g/min; or at least 0.7 mmol/g/min; or at least 0.8 mmol/g/min; or at least 0.9 mmol/g/min; or at least 1.0 mmol/g/min; or at least 1.2 mmol/g/min; or at least 1.5 mmol/g/min; lactate dehydrogenase is upregulated. As such, the invention provides a method of producing lactate by microbial fermentation of a substrate by upregulation of lactate dehydrogenase.

It is considered that products such as lactate can be produced by the Wood-Ljungdahl pathway in carboxydotrophic micro-organisms such as *Clostridium autoethanogenum* by fermentation of alternative substrates such as carbohydrates. Thus, in particular embodiments, the method includes fermentation of substrates comprising carbohydrate, such as fructose or xylose, to produce products including lactic acid.

It is further considered that alternative substrates, such as a carbohydrate substrate and a gaseous substrate comprising CO, can be switched during microbial production of lactic acid, without deleterious effect. In addition, it is contemplated that substrates could be alternated, for example when one substrate is unavailable, the alternate substrate is provided such that the micro-organism continues to produce lactic acid.

In accordance with the results obtained, in one embodiment of the invention, lactic acid is produced by microbial fermentation of a substrate comprising carbohydrate. In another embodiment of the invention, a substrate comprising carbon monoxide, preferably a gaseous substrate comprising CO, is converted into various products including lactic acid, by *Clostridium autoethanogenum*.

It is contemplated that the lactic acid produced in accordance with the methods of the invention may be readily recovered using separation techniques known in the art.

The invention is generally described herein in relation to preferred embodiments of the invention which utilise *Clostridium autoethanogenum* and/or produce lactic acid. However, it should be appreciated that alternative micro-organisms may be substituted for *C. autoethanogenum* such as alternative micro-organisms which ferment substrates comprising CO, for example *C. Ijungdahlii, C. ragsdalei* and *C. carboxydivorans*. Other carboxydotrophic microorganisms that produce products via the Wood Ljungdahl pathway may also be used.

Method

In one embodiment, the invention provides a method for the production of lactic acid by microbial fermentation. In a preferred embodiment the method comprises at least the step of anaerobically fermenting a substrate comprising CO, preferably a gaseous substrate comprising CO, to obtain lactic acid.

In a particular embodiment of the invention, the method includes the steps of:
(a) providing a substrate comprising CO, preferably a gaseous substrate comprising CO;
(b) in a bioreactor containing a culture of one or more micro-organisms anaerobically fermenting the substrate to produce lactic acid.

In another embodiment, the invention provides a method of increasing efficiency of lactic acid production by fermentation, the method including:
(a) providing a substrate comprising CO;
(b) in a bioreactor containing a culture of one or more micro-organisms, anaerobically fermenting the substrate to produce lactic acid.

In particular embodiments, the substrate comprising CO is provided at a level sufficient to produce significant amounts of lactic acid, such as at least 0.05 g/L of fermentation media, or at least 0.1 g/L, or at least 0.2 g/L, or at least 0.4 g/L, or at least 0.6 g/L, or at least 0.8 g/L, or at least 1 g/L. In certain embodiments, CO is provided at a level sufficient to produce lactic acid at a rate of at least 0.5 g/L/day; or at least 1 g/L/day. In particular embodiments, CO is provided such that a specific uptake rate of at least 0.4 mmol/g/min; or at least 0.5 mmol/g/min; or at least 0.6 mmol/g/min; or at least 0.7 mmol/g/min; or at least 0.8 mmol/g/min; or at least 0.9 mmol/g/min; or at least 1.0 mmol/g/min; or at least 1.2 mmol/g/min; or at least 1.5 mmol/g/min is maintained. Those skilled in the art will appreciate methods of supplying CO, particularly gaseous CO, such that the required uptake rate is achieved. However, by way of example, factors such as increasing gas hold-up in a fermentation media will increase the amount of CO available for conversion to products by the microbial culture. Gas hold-up can typically be increased by mechanical means, such as increasing agitation in a CSTR. Furthermore, supplying CO at a faster rate or a higher partial pressure will also increase the CO availability in a fermentation broth.

In another embodiment, the method involves fermentation of a substrate comprising carbohydrate by *Clostridium autoethanogenum* to produce lactic acid.

In certain embodiments of the invention, the method further includes the step of capturing or recovering the lactic acid produced.

Micro-Organisms

In embodiments of the invention the one or more micro-organisms used in the fermentation is one or more carboxydotrophic micro-organisms. In particular embodiments, the microorganisms are Clostridia, such as *Clostridium autoethanogenum*. In particular embodiments, the micro-organism ferments a substrate comprising CO via the Wood-Ljungdahl pathway. In a preferred embodiment the *Clostridium autoethanogenum* is a *Clostridium autoethanogenum* having the identifying characteristics of the strain deposited at the German Resource Centre for Biological Material (DSMZ) under the identifying deposit number 19630. In another embodiment the *Clostridium autoethanogenum* is a *Clostridium autoethanogenum* having the identifying characteristics of DSMZ deposit number DSMZ 10061.

Culturing of the bacteria used in a method of the invention may be conducted using any number of processes known in the art for culturing and fermenting substrates using anaerobic bacteria. Exemplary techniques are provided in the "Examples" section of this document. By way of further example, those processes generally described in the following articles using gaseous substrates for fermentation may be utilised: K. T. Klasson, M. D. Ackerson, E. C. Clausen and J. L. Gaddy (1991). Bioreactors for synthesis gas fermentations resources. Conservation and Recycling, 5; 145-165; K. T. Klasson, M. D. Ackerson, E. C. Clausen and J. L. Gaddy (1991). Bioreactor design for synthesis gas fermentations. Fuel. 70. 605-614; K. T. Klasson, M. D. Ackerson, E. C. Clausen and J. L. Gaddy (1992). Bioconversion of synthesis gas into liquid or gaseous fuels. Enzyme and Microbial Technology. 14; 602-608; J. L. Vega, G. M. Antorrena, E. C. Clausen and J. L. Gaddy (1989). Study of Gaseous Substrate Fermentation: Carbon Monoxide Conversion to Acetate. 2. Continuous Culture. Biotech. Bioeng. 34. 6. 785-793; J. L. Vega, E. C. Clausen and J. L. Gaddy (1989). Study of gaseous substrate fermentations: Carbon monoxide conversion to acetate. 1. Batch culture. Biotechnology and Bioengineering. 34. 6. 774-784; and, J. L. Vega, E. C. Clausen and J. L. Gaddy (1990). Design of Bioreactors for Coal Synthesis Gas Fermentations. Resources, Conservation and Recycling. 3. 149-160. Methods for culturing bacteria on substrates comprising carbohydrates are also well known in the art.

Substrates

In one embodiment of the invention, lactic acid is produced by microbial fermentation of a substrate comprising carbohydrate using *Clostridium autoethanogenum*. It will be appreciated there are many examples of carbohydrates suitable for fermentation known in the art and many examples of the types of processes used to ferment the carbohydrate substrate. By way of example, suitable substrates may include, but are not limited to, monosaccharides such as glucose and fructose, oligosaccharides such as sucrose or lactose, polysaccharides, such as cellulose or starch. Although it is contemplated that any of these carbohydrate substrates (and mixtures thereof) are suitable in the present invention, preferred carbohydrate substrates are fructose and sucrose (and mixtures thereof).

Those skilled in the art will appreciate fermentable sugars may be obtained from cellulosic and lignocellulosic biomass through processes of pre-treatment and saccharification, as described, for example, in US20070031918. Biomass refers to any cellulose or lignocellulosic material and includes materials comprising cellulose, and optionally further comprising hemicellulose, lignin, starch, oligosaccharides and/or monosaccharides. Biomass includes, but is not limited to bioenergy crops, agricultural residues, municipal solid waste, industrial solid waste, sludge from paper manufacture, yard waste, wood and forestry waste. However, in exemplary embodiments of the invention commercially available fructose is used as the carbon and energy source for the fermentation.

In a particular embodiment, a substrate comprising carbon monoxide, preferably a gaseous substrate comprising carbon monoxide is used in the methods of the invention. The gaseous substrate may be a waste gas obtained as a by-product of an industrial process, or from some other source such as from combustion engine (for example automobile) exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. Depending on the composition of the gaseous substrate comprising carbon monoxide, it may also be desirable to treat it to remove any undesired impurities, such as dust particles before introducing it to the fermentation. For example, the gaseous substrate may be filtered or scrubbed using known methods.

In other embodiments of the invention, the gaseous substrate comprising carbon monoxide may be sourced from the gasification of biomass. The process of gasification involves partial combustion of biomass in a restricted supply of air or oxygen. The resultant gas typically comprises mainly CO and $H_2$, with minimal volumes of $CO_2$, methane, ethylene and ethane. For example, biomass by-products obtained during the extraction and processing of foodstuffs such as sugar from sugarcane, or starch from maize or grains, or non-food biomass waste generated by the forestry industry may be gasified to produce a CO-containing gas suitable for use in the present invention.

The CO-containing substrate will typically contain a major proportion of CO, such as at least about 20% to about 100% CO by volume, from 40% to 95% CO by volume, from 40% to 60% CO by volume, and from 45% to 55% CO by volume. In particular embodiments, the substrate comprises about 25%, or about 30%, or about 35%, or about 40%, or about 45%, or about 50% CO, or about 55% CO, or about 60% CO by volume. Substrates having lower concentrations of CO, such as 6%, may also be appropriate, particularly when $H_2$ and $CO_2$ are also present.

In particular embodiments, CO is supplied at a level sufficient for lactic acid production to occur. In particular embodiments, CO is provided such that a specific uptake rate of at least 0.4 mmol/g/min; or at least 0.5 mmol/g/min; or at least 0.6 mmol/g/min; or at least 0.7 mmol/g/min; or at least 0.8 mmol/g/min; or at least 0.9 mmol/g/min; or at least 1.0 mmol/g/min; or at least 1.2 mmol/g/min; or at least 1.5 mmol/g/min is maintained.

Those skilled in the art will appreciate methods of supplying CO, particularly gaseous CO, such that the required uptake rate is achieved. Higher rates of CO uptake can be achieved by improving mass transfer of the system, wherein the amount of CO dissolved in a typically aqueous fermentation broth increases. However, by way of example, factors such as increasing gas hold-up in a fermentation media will increase the amount of CO available for conversion to products by the microbial culture. Those skilled in the art will appreciate methods of increasing gas hold-up. However, by way of non-limiting example, gas hold-up is typically increased by mechanical means such as increasing agitation in a CSTR. Furthermore, supplying CO at a faster rate or a higher partial pressure will also increase the CO availability in a fermentation broth.

It is not necessary for the gaseous substrate to contain any hydrogen, however this is not considered detrimental to lactic acid production. The gaseous substrate may also contain some $CO_2$ for example, such as about 1% to about 80% by volume, or 1% to about 30% by volume. In one embodiment it contains about 5% to about 10% by volume. In another embodiment the gaseous substrate contains approximately 20% $CO_2$ by volume.

Typically, the carbon monoxide will be added to the fermentation reaction in a gaseous state. However, the invention should not be considered to be limited to addition of the substrate in this state. For example, the carbon monoxide could be provided in a liquid. For example, a liquid may be saturated with a carbon monoxide containing gas and then that liquid added to a bioreactor. This may be achieved using standard methodology. By way of example a microbubble dispersion generator (Hensirisak et. al. Scale-up of microbubble dispersion generator for aerobic fermentation; *Applied Biochemistry and Biotechnology Volume* 101, *Number* 3/*October,* 2002) could be used.

Media

It will be appreciated that for growth of the bacteria and substrate to lactate fermentation to occur, in addition to the substrate, a suitable nutrient medium will need to be fed to the bioreactor. A nutrient medium will contain components, such as vitamins and minerals, sufficient to permit growth of the micro-organism used. Anaerobic media suitable for the growth of carboxydotrophic Clostridia such as *Clostridium autoethanogenum* are known in the art, as described for example by Abrini et al (*Clostridium autoethanogenum*, sp. November, An Anaerobic Bacterium That Produces Ethanol From Carbon Monoxide; *Arch. Microbiol.,* 161: 345-351 (1994)). The "Examples" section herein after provides further examples of suitable media.

Fermentation Conditions

The fermentation should desirably be carried out under appropriate conditions for the substrate to lactic acid fermentation to occur. Reaction conditions that should be considered include temperature, media flow rate, pH, media redox potential, agitation rate (if using a continuous stirred tank reactor), inoculum level, maximum substrate concentrations and rates of introduction of the substrate to the bioreactor to ensure that substrate level does not become limiting, and maximum product concentrations to avoid product inhibition. Examples of fermentation conditions suitable for anaerobic fermentation of a substrate comprising CO are detailed in WO2007/117157, WO2008/115080, WO2009/022925 and WO2009/064200, the disclosure of which are incorporated herein by reference. It is recognised the fermentation conditions reported therein can be readily modified in accordance with the methods of the instant invention.

The inventors have determined that, in one embodiment where pH is not controlled, there does not appear to be a deleterious effect on lactic acid production.

Bioreactor

Fermentation reactions may be carried out in any suitable bioreactor as described previously herein. In some embodiments of the invention, the bioreactor may comprise a first, growth reactor in which the micro-organisms are cultured, and a second, fermentation reactor, to which broth from the growth reactor is fed and in which most of the fermentation product (lactic acid, for example) is produced.

Product Recovery

The fermentation will result in fermentation broth comprising lactate and, possibly, one or more by-products, such as ethanol or acetate, as well as bacterial cells in a liquid nutrient media. Lactate or lactic acid can be removed from the typically aqueous fermentation broth by any known method. For example, conventional fermentation process produces calcium lactate precipitate, which can be collect and re-acidified.

Alternatively, membrane techniques, such as electrodialysis can be sued to separate lactate. Low concentrations of lactate can be separated from a fermentation broth by applying a suitable potential across a selective ion permeable membrane. Other suitable techniques include nanofiltration, wherein monovalent ions can selectively pass through a membrane under pressure.

Other desirable products, such as acetate and/or ethanol can be removed form the fermentation broth using any recovery means known in the art, such as methods described in WO2007/117157, which is fully incorporated herein by reference.

The invention will now be described in more detail with reference to the following non-limiting examples.

EXAMPLES

Materials and Methods

| Solution A | | | |
|---|---|---|---|
| $NH_4Ac$ | 3.083 g | KCl | 0.15 g |
| $MgCl_2 \cdot 6H_2O$ | 0.61 g | NaCl | 0.12 g |
| $CaCl_2 \cdot 2H_2O$ | 0.294 g | Distilled Water | Up to 1 L |

| Solution(s) B | | | |
|---|---|---|---|
| Component/0.1 M solution (aq) | Quantity/ml into 1 L media | Component/0.1 M solution (aq) | Quantity/ml into 1 L media |
| $FeCl_3$ | 1 ml | $Na_2WO_4$ | 0.1 ml |
| $CoCl_2$ | 0.5 ml | $ZnCl_2$ | 0.1 ml |
| $NiCl_2$ | 0.5 ml | $Na_2MoO_4$ | 0.1 ml |
| $H_3BO_3$ | 0.1 ml | | |

| Solution C | | | |
|---|---|---|---|
| Biotin | 20.0 mg | Calcium D-(*)-pantothenate | 50.0 mg |
| Folic acid | 20.0 mg | Vitamin B12 | 50.0 mg |
| Pyridoxine•HCl | 10.0 mg | p-Aminobenzoic acid | 50.0 mg |
| Thiamine•HCl | 50.0 mg | Thioctic acid | 50.0 mg |
| Riboflavin | 50.0 mg | Distilled water | To 1 Litre |
| Nicotinic acid | 50.0 mg | | |

-continued

Solution D

| | | | |
|---|---|---|---|
| Solution A | 50 ml | Solution C | 10 ml |
| Solution B | 10 × conc | Distilled Water | Up to 1 L |
| $Na_2S_x$ | 2 ml | | |

Solution E

| | | | |
|---|---|---|---|
| Solution B | 10 × conc | $Na_2S_x$ | 2 ml |

Solution F

| | | | |
|---|---|---|---|
| $NH_4Ac$ | 0.5 g | KCl | 0.15 g |
| $MgCl_2 \cdot 6H_2O$ | 0.5 g | NaCl | 0.2 g |
| $CaCl_2 \cdot 2H_2O$ | 0.26 g | $NaH_2PO_4$ | 2.04 g |
| Solution G | 10 ml | Solution H | 10 ml |
| Resazurin (2 g/L stock) | 1 ml | $FeCL_3$ (5 g/L stock) | 2 ml |
| Cysteine HCL | 0.5 g | Agar | optional |
| Distilled Water | Up to 1 L | | |

Solution G—Composite Mineral Stock Solution

| | | | |
|---|---|---|---|
| Nitrolotriacetic acid | 1.5 g | $MgSO_4 \cdot 7H_2O$ | 3.0 g |
| $MnSO_4 \cdot H_2O$ | 0.5 g | NaCl | 1.0 g |
| $FeSO_4 \cdot 7H_2O$ | 0.1 g | $Fe(SO_4)_2(NH_4)_2 \cdot 6H_2O$ | 0.8 g |
| $CoCl_2 \cdot 6H_2O$ | 0.2 g | $ZnSO_4 \cdot 7H_2O$ | 0.2 g |
| $CuCl_2 \cdot 2H_2O$ | 0.02 g | $AlK(SO_4)_2 \cdot 12H_2O$ | 0.02 g |
| $H_3BO_3$ | 0.30 g | $NaMoO_4 \cdot 2H_2O$ | 0.03 g |
| *$Na_2SeO_3$ | 0.02 g | *$NiCl_2 \cdot 6H_2O$ | 0.02 g |
| $Na_2WO_4 \cdot 6H_2O$ | 0.02 g | Distilled Water | Up to 1 L |

Solution H—Genthner B-Vitamin Solution

| | | | |
|---|---|---|---|
| Thiamine hydrochloride (Vitamin B1) | 50.0 mg | Riboflavin (Vitamin B2) | 50.0 mg |
| Nicotinic acid (Niacin or Vitamin B3) | 50.0 mg | Pantothenic acid (Vitamin B5) | 50.0 mg |
| Pyridoxine hydrochloride (Vitamin B6) | 10.0 mg | Biotin (Vitamin B7) | 20.0 mg |
| Folic acid (Vitamin B9) | 20.0 mg | 4-Aminobenzoic acid (PABA or Vitamin B10) | 50.0 mg |
| Cyanocobalamin (Vitamin B12) | 50.0 mg | Distilled water | To 1 Litre |
| Lipoic acid (Thioctic acid) | 50.0 mg | | |

Preparation of $Na_2S_x$

A 500 ml flask was charged with $Na_2S$ (93.7 g, 0.39 mol) and 200 ml $H_2O$. The solution was stirred until the salt had dissolved and sulfur (25 g, 0.1 mol) was added under constant $N_2$ flow. After 2 hours stirring at room temperature, the "$Na_2S_x$" solution (approx 4M with respect to [Na] and approx 5M with respect to [S]), now a clear reddish brown liquid, was transferred into $N_2$ purged serum bottles, wrapped in aluminium foil.

Preparation of Cr (II) Solution

A 1 L three necked flask was fitted with a gas tight inlet and outlet to allow working under inert gas and subsequent transfer of the desired product into a suitable storage flask. The flask was charged with $CrCl_3 \cdot 6H_2O$ (40 g, 0.15 mol), zinc granules [20 mesh] (18.3 g, 0.28 mol), mercury (13.55 g, 1 mL, 0.0676 mol) and 500 mL of distilled water. Following flushing with $N_2$ for one hour, the mixture was warmed to about 80° C. to initiate the reaction. Following two hours of stirring under a constant $N_2$ flow, the mixture was cooled to room temperature and continuously stirred for another 48 hours by which time the reaction mixture had turned to a deep blue solution. The solution was transferred into $N_2$ purged serum bottles and stored in the fridge for future use.

Bacteria:

In a preferred embodiment the *Clostridium autoethanogenum* is a *Clostridium autoethanogenum* having the identifying characteristics of the strain deposited at the German Resource Centre for Biological Material (DSMZ) under the identifying deposit number 10061. In another embodiment the *Clostridium autoethanogenum* is a *Clostridium autoethanogenum* having the identifying characteristics of DSMZ deposit number DSMZ 23693.

Sampling and Analytical Procedures

Media samples were taken from the CSTR reactor at intervals over periods up to 10 days. Each time the media was sampled care was taken to ensure that no gas was allowed to enter into or escape from the reactor.

HPLC:

HPLC System Agilent 1100 Series. Mobile Phase: 0.0025N Sulfuric Acid. Flow and pressure: 0.800 mL/min. Column: Alltech IOA; Catalog #9648, 150×6.5 mm, particle size 5 μm. Temperature of column: 60° C. Detector: Refractive Index. Temperature of detector: 45° C.

Method for Sample Preparation:

400 μL of sample and 50 μL of 0.15M $ZnSO_4$ and 50 μL of 0.15M $Ba(OH)_2$ are loaded into an Eppendorf tube. The tubes are centrifuged for 10 min. at 12,000 rpm, 4° C. 200 μL of the supernatant are transferred into an HPLC vial, and 5 μL are injected into the HPLC instrument.

Gas Chromatography:

Gas Chromatograph HP 5890 series II utilizing a Flame Ionization Detector. Capillary GC Column: EC1000-Alltech EC1000 30 m×0.25 mm×0.25 um. The Gas Chromatograph was operated in Split mode with a total flow of hydrogen of 50 mL/min with 5 mL purge flow (1:10 split), a column head pressure of 10 PIS resulting in a linear velocity of 45 cm/sec. The temperature program was initiated at 60° C., held for 1 minute then ramped to 215° C. at 30° C. per minute, then held for 2 minutes. Injector temperature was 210° C. and the detector temperature was 225° C.

Method for Sample Preparation:

500 μL sample is centrifuged for 10 min at 12,000 rpm, 4° C. 100 μL of the supernatant is transferred into an GC vial containing 200 μL water and 100 μL of internal standard spiking solution (10 g/L propan-1-ol, 5 g/L iso-butyric acid, 135 mM hydrochloric acid). 1 μL of the solution is injected into the GC instrument.

Cell Density:

Cell density was determined by counting bacterial cells in a defined aliquot of fermentation broth. Alternatively, the absorbance of the samples was measured at 600 nm (spectrophotometer) and the dry mass determined via calculation according to published procedures.

Example 1

Batch Fermentation in CSTR 1.5 liters of media solution A was aseptically and anaerobically transferred into a 2 L CSTR vessel, and continuously sparged with $N_2$. Once transferred to the fermentation vessel, the reduction state and pH of the transferred media could be measured directly via probes. The media was heated to 37° C. and stirred at 400 rpm and resazurin (2 g/L) was added. 2.25 ml of H3P04 85% was added to obtain a 30 mM solution and the pH was adjusted to 5.3 using NH4OH. The media was then reduced further to −150 mV by the addition of 0.3M Cr(II)chloride solution.

Polysulfide solution (4.5M) was added to the solution, and the pH adjusted to 5.5 using NH4OH. $N_2$ was continuously sparged through the solution following the addition of the polysulfide solution. Metal ions were added according to solution B and 15 ml of solution C was added.

Figure 1:
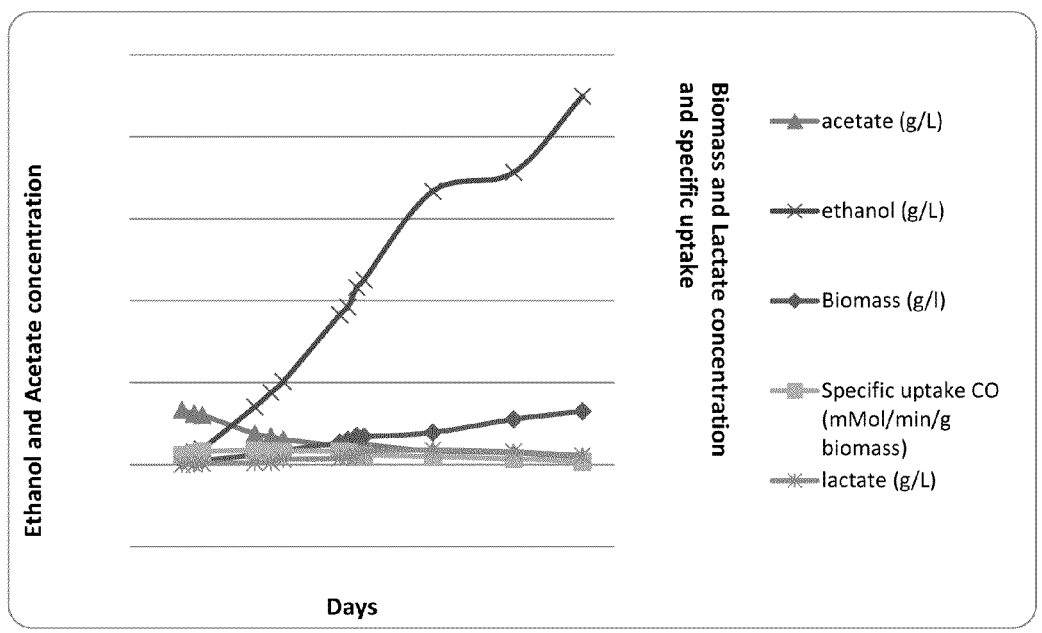
FIG. 1 is graph demonstrating lactate production according a method of the invention as described in example 1.

Prior to inoculation, the gas was switched to a pre-mixed blend of 50% CO, 2% $H_2$, 19% $CO_2$, and 29% $N_2$, which was continuously sparged into the fermentation broth throughout the experiment. An actively growing *Clostridium autoethanogenum* culture was inoculated into the CSTR at a level of approximately 5% (v/v). During these experiments, the pH was adjusted and/or maintained by a controller through the automated addition of buffers (0.5 M NaOH or 2N $H_2SO_4$). Metabolite production and microbial growth can be seen in FIG. 1. FIG. 1 shows that typical metabolites including ethanol are produced throughout the microbial growth phase. In addition, lactate is produced through fermentation of CO by *Clostridium autoethanogenum*. However, lactate is produced by the microbial culture when substrate is supplied such that the specific uptake is maintained above 0.5 mmol/g biomass/minute.

Example 2

Batch Fermentation in CSTR 1.5 liters of the media solution A was aseptically and anaerobically transferred into a 2 L CSTR vessel, and continuously sparged with $N_2$. Once transferred to the fermentation vessel, the reduction state and pH of the transferred media could be measured directly via probes. The media was heated to 37° C. and stirred at 400 rpm and resazurin (2 g/L) was added. 2.025 ml of H3P04 85% was added to obtain a 30 mM solution and the pH was adjusted to 5.3 using NH4OH. The media was then reduced further to −150 mV by the addition of 0.3M Cr(II)chloride solution.

Polysulfide solution (3.5M) was added to the solution. $N_2$ was continuously sparged through the solution following the addition of the polysulfide solution. Prior to inoculation, the gas was switched to a pre-mixed blend of 54% CO, 3% $H_2$, 20% CO2, and 23% $N_2$, which was continuously sparged into the fermentation broth throughout the experiment. 150 ml of solution D was added and 13.5 ml of solution C was added. An actively growing *Clostridium autoethanogenum* culture was inoculated into the CSTR at a level of approximately 5% (v/v). During these experiments, the pH was adjusted and/or maintained by a controller through the automated addition of buffers (0.5 M NaOH or 2N $H_2SO_4$).

Figure 2:
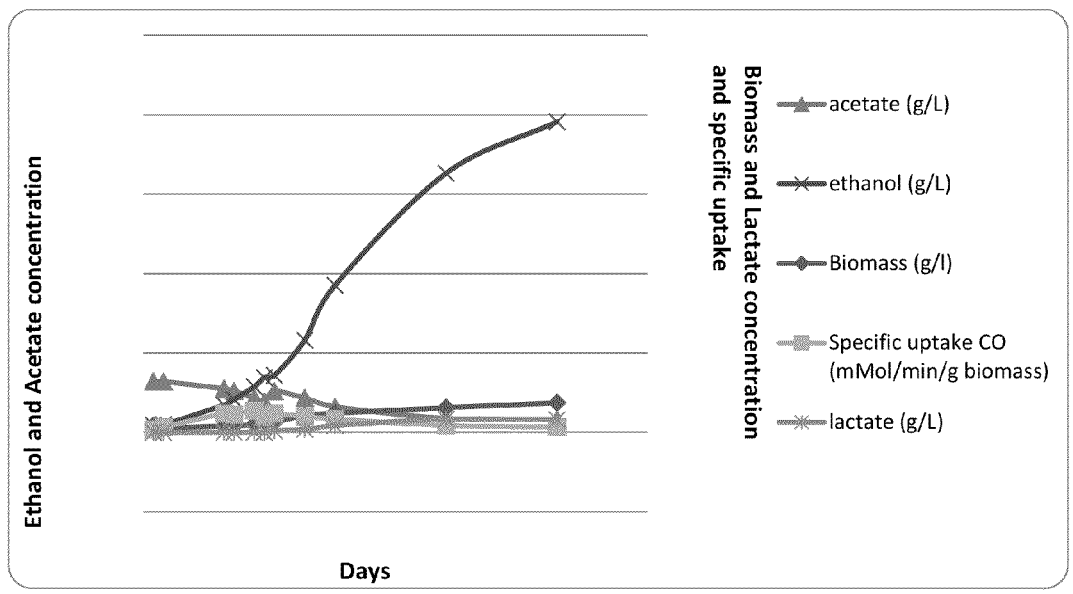
FIG. 2 is a graph demonstrating lactate production according a method of the invention as described in example 2.

Metabolite production and microbial growth can be seen in FIG. 2. FIG. 2 shows that typical metabolites including ethanol are produced throughout the microbial growth phase. However, lactate is produced by the microbial culture when substrate is supplied such that the specific uptake is maintained above 0.5 mmol/g biomass/minute. Between approximately day 1.0 and 1.5, the rate of lactate production was at least 1.0 g/L/day.

Example 3

Continuous Fermentation in CSTR 1 liter of the media solution was aseptically and anaerobically transferred into a 1 L CSTR vessel, and continuously sparged with $N_2$. Once transferred to the fermentation vessel, the reduction state and pH of the transferred media could be measured directly via probes. The media was heated to 37° C. and stirred at 400 rpm. 1.2 ml of H3P04 85% was added to obtain a 30 mM solution and the pH was adjusted to 5.3 using NH4OH. 8 ml of solution C was added. The media was then reduced further to −150 mV by the addition of 0.3M Cr (II) chloride solution. Resazurin was then added (2 g/L).

Polysulfide solution (6M) was added to the solution. $N_2$ was continuously sparged through the solution following the addition of the polysulfide solution. Prior to inoculation, the gas was switched to a pre-mixed blend of 70% CO, 1% $H_2$, 15% CO2, and 14% $N_2$, which was continuously sparged into the fermentation broth throughout the experiment. 80 ml of solution E was added. An actively growing *Clostridium autoethanogenum* culture was inoculated into the CSTR at a level of approximately 5% (v/v). During these experiments, the pH was adjusted and/or maintained by a controller through the automated addition of buffers (0.5 M NaOH or 2N $H_2SO_4$).

Figure 3:
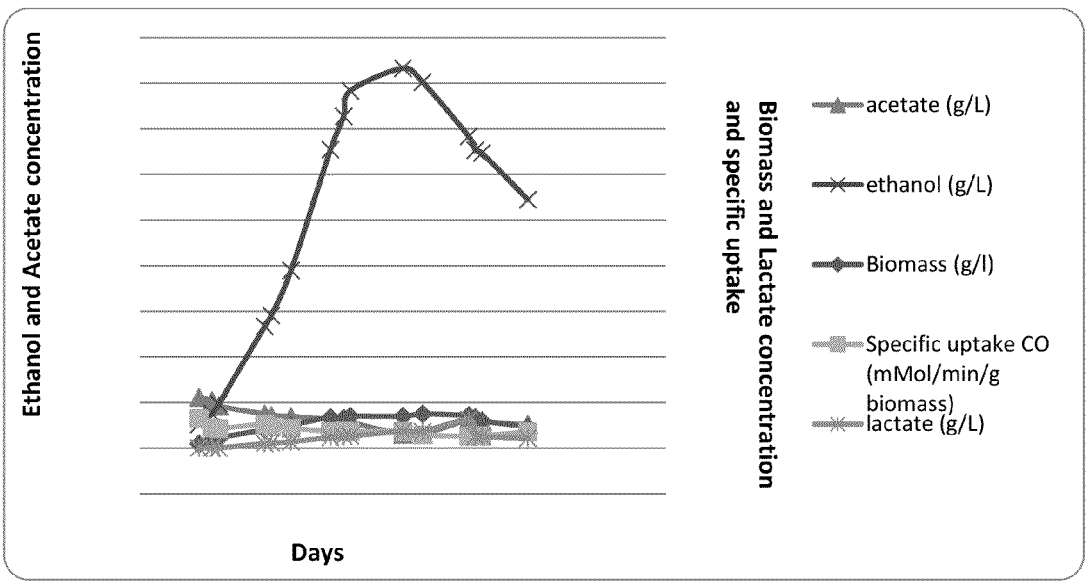
FIG. 3 is a graph demonstrating lactate production according a method of the invention as described in example 3.

Metabolite production and microbial growth can be seen in FIG. 3. FIG. 3 shows that typical metabolites including ethanol are produced throughout the microbial growth phase. However, lactate is produced by the microbial culture when substrate is supplied such that the specific uptake is maintained above 0.5 mmol/g biomass/minute. The microbial culture continues to produce lactate even when growth and ethanol production. However, lactate production ceases when the specific uptake drops below 0.5 mmol/g/min.

Example 4

Continuous Fermentation in CSTR 1.5 liters of media solution A having a $MgCl_2.6H_2O$ content of 0.407 g was aseptically and anaerobically transferred into a 2 L CSTR vessel, and continuously sparged with $N_2$. Once transferred to the fermentation vessel, the reduction state and pH of the transferred media could be measured directly via probes. The media was heated to 37° C. and stirred at 400 rpm and resazurin (2 g/L) was added. 0.56 ml of H3P04 85% was added to obtain a 5 mM solution and the pH was adjusted to 5.3 using NH4OH.

Iron (0.1M), Nickel (0.05M) and Zinc (0.005M) were added to the solution, as was 0.01M (B, Mn, Co, Se, Mo) and 0.01M Tungsten solution. 15 ml of B-Vitamin was also added. The media was then reduced further to −200 mV by the addition of 0.3M Cr(II)chloride solution Prior to inoculation, the gas was switched to a pre-mixed blend of 10% CO, 15% $H_2$, 75% RMG, which was continuously sparged into the fermentation broth throughout the experiment. An actively growing *Clostridium autoethanogenum* culture was inoculated into the CSTR at a level of approximately 5% (v/v). During these experiments, the pH was adjusted and/or maintained by a controller through the automated addition of buffers (0.5 M NaOH or 2N $H_2SO_4$).

Figure 4:
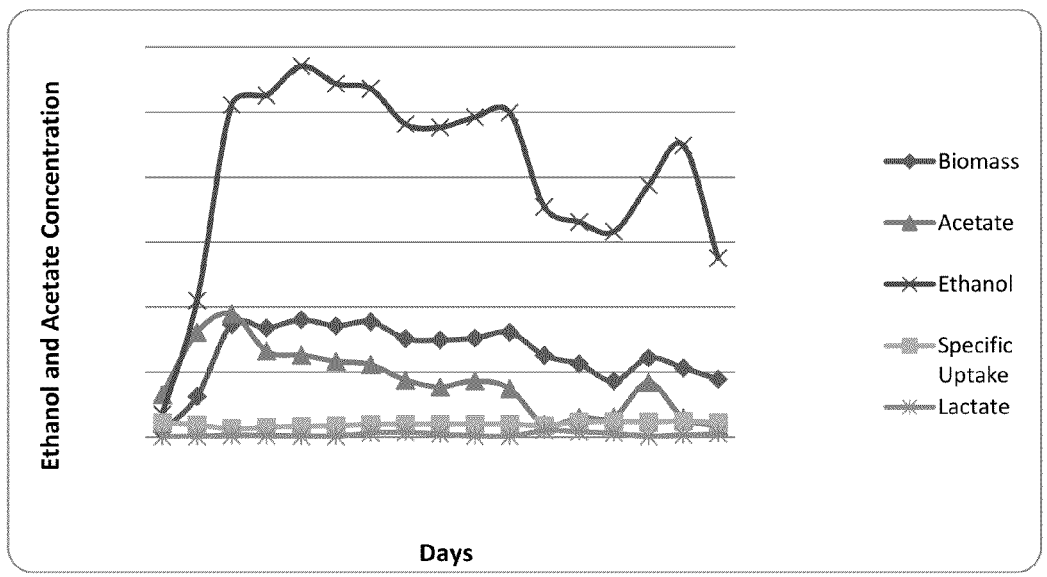
FIG. 4 is a graph demonstrating lactate production according a method of the invention as described in example 4.

Metabolite production and microbial growth can be seen in FIG. 4. FIG. 4 shows that typical metabolites including ethanol are produced throughout the microbial growth phase. However, lactate is produced by the microbial culture when substrate is supplied such that the specific uptake is maintained above 0.6 mmol/g biomass/minute.

Example 5

Effect of Lactic Acid Concentration on Growth and Metabolite Production

The effect of lactic acid concentrations on acetate production and biomass was examined using serum bottles. One liter of Solution F was made with an addition of 1 g/l of yeast extract. The media was split into five aliquots of 200 ml, and to each, DL-Lactic acid was added to a different final concentration. This was followed by pH adjustment to 5.5 using 5M NaOH. The concentrations tested were 0 g/l, 0.3 g/l, 0.6 g/l, 1 g/l and 5 g/l.

The media was bubbled with N2 for at least one hour and dispensed into serum bottles in 50 ml aliquots under anaerobic conditions. Serum bottles were autoclaved for 30 mins at 121° C.

A microbial culture comprising *C. autoethanogenum* was grown in the prepared media under a mill gas headspace (30 psig) at 37° C. for three days or until exponential growth is reached (OD600 approximately 0.5)

The serum bottles were inoculated with 2.5 ml of culture, pressurised to 30 psig with mill gas and incubated at 37° C., shaking. OD600 change and metabolite production were monitored through daily sampling.

The experimental setup was carried out in a similar fashion as discussed above, using range of lactic acid concentrations. The concentrations tested were 0 g/l, 1 g/l, 2 g/l, 3 g/l, 4 g/l and 20 g/l.

The cultures were then monitored over seven (7) days to determine the growth of the culture in biomass, the amount of acetate produced by the culture and the amount of Lactic acid taken up by the culture.

At concentrations of between 0.3 g/l and 1 g/l the amount of biomass observed was comparable to the culture with no lactic acid. Concentrations of between 2 g/l and 4 g/l showed reduced biomass when compared to zero concentration lactic acid, and no growth was observed in cultures comprising 5 g/l or more of lactic acid.

Correspondingly, the serum bottles having a lactic acid concentration of 5 g/l or greater demonstrated no acetate production and no lactic acid uptake.

The invention has been described herein with reference to certain preferred embodiments, in order to enable the reader to practice the invention without undue experimentation. Those skilled in the art will appreciate that the invention is susceptible to variations and modifications other than those specifically described. It is to be understood that the invention includes all such variations and modifications. Furthermore, titles, headings, or the like are provided to enhance the reader's comprehension of this document, and should not be read as limiting the scope of the present invention.

The entire disclosures of all applications, patents and publications, cited above and below, if any, are hereby incorporated by reference.

The reference to any prior art in this specification is not, and should not be taken as, an acknowledgment or any form of suggestion that that prior art forms part of the common general knowledge in the United States of America or any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

What I claim is:

1. A method of producing lactate by microbial fermentation, said method comprising:
    continuously passing a gaseous substrate comprising CO to a bioreactor comprising a culture of a *Clostridium autoethanogenum* bacterium and anaerobically fermenting the substrate to produce lactate; wherein the *Clostridium autoethanogenum* bacterium comprises at least one lactate dehydrogenase gene and the lactate dehydrogenase gene is upregulated; and
    wherein the gaseous substrate comprising CO is provided such that a specific rate of CO uptake of at least 0.4 mmol CO/gram dry cells weight of bacteria/minute by the culture is maintained and lactate is produced at a productivity greater than 0.2 g/L/per day.

2. The method of claim 1 wherein the substrate is provided at a level sufficient to maintain a specific CO uptake rate of at least 0.6 mmol CO/gram dry cells weight of bacteria/minute.

3. The method of claim 1, wherein the gaseous substrate comprises at least 15% to about 100% CO by volume.

4. The method of claim 1, wherein the gaseous substrate comprises a gas obtained as a by-product from an industrial process.

5. The method of claim 1 wherein the substrate is provided at a level sufficient to maintain a specific CO uptake rate of at least 0.8 mmol CO/gram dry cells weight of bacteria/minute.

6. The method of claim 1 wherein the lactate is produced at a productivity greater than 0.3 g/L/per day.

7. The method of claim 1 wherein the lactate is produced at a productivity greater than 0.5 g/L/per day.

8. The method of claim 1 wherein the *Clostridium autoethanogenum* is the *Clostridium autoethanogenum* strain deposited at the German Collection of Microorganisms and Cell Cultures (DSMZ) under the accession number DSM 19630.

\* \* \* \* \*